(12) United States Patent
Edwards (10) Patent No.: US 12,007,030 B2
(45) Date of Patent: Jun. 11, 2024

(54) TWO POSITION MEDICAL HANDPIECE SEAL

(71) Applicant: GYRUS ACMI, INC., Southborough, MA (US)

(72) Inventor: Kevin Cooper Edwards, Olive Branch, MS (US)

(73) Assignee: Gyrus ACMI, Inc., Westborough, MA (US)

( * ) Notice: Subject to any disclaimer, the term of this patent is extended or adjusted under 35 U.S.C. 154(b) by 758 days.

(21) Appl. No.: 17/026,366

(22) Filed: Sep. 21, 2020

(65) Prior Publication Data

US 2021/0102629 A1 Apr. 8, 2021

Related U.S. Application Data

(60) Provisional application No. 62/960,273, filed on Jan. 13, 2020, provisional application No. 62/910,519, filed on Oct. 4, 2019.

(51) Int. Cl.

| *F16J 15/34* | (2006.01) |
|---|---|
| *A61B 17/16* | (2006.01) |
| *F16J 15/00* | (2006.01) |
| A61B 17/32 | (2006.01) |
| A61B 17/3207 | (2006.01) |
| A61F 11/20 | (2022.01) |

(52) U.S. Cl.
CPC ......... *F16J 15/3436* (2013.01); *F16J 15/002* (2013.01); *A61B 17/1622* (2013.01); *A61B 17/1631* (2013.01); *A61B 17/32002* (2013.01); *A61B 2017/320032* (2013.01); *A61B 17/320758* (2013.01); *A61F 11/20* (2022.01)

(58) Field of Classification Search
CPC ............ A61B 17/1622; A61B 17/1631; A61B 17/32002; A61B 17/320758; A61B 2017/320032; A61F 11/20; F16J 15/3436; F16J 15/002; F16J 15/008
See application file for complete search history.

(56) References Cited

U.S. PATENT DOCUMENTS

| 4,408,765 | A | * | 10/1983 | Adelmann, Jr. | ....... F16J 15/006 277/408 |
|---|---|---|---|---|---|
| 6,142,478 | A | * | 11/2000 | Pecht | ................... F16J 15/3484 277/400 |
| 10,245,042 | B2 | | 4/2019 | Koltz | |

(Continued)

*Primary Examiner* — Gilbert Y Lee
(74) *Attorney, Agent, or Firm* — Schwegman Lundberg & Woessner, P.A.

(57) ABSTRACT

A two-position handpiece coupling seal is provided. The two-position handpiece coupling seal includes a neck disposed at a first end that is configured to receive an implement. The two-position handpiece coupling seal has a first seal disposed about the neck of the two-position handpiece coupling seal. The first seal is configured to engage with a surface of a housing of a handpiece that uses the two-position coupling seal in a first position. The two-position handpiece coupling seal has a second seal disposed about a bore of the two-position handpiece coupling seal at a second end of the two-position handpiece coupling seal opposite the first end. The bore is configured to receive a driveshaft and the second seal is configured to sealingly engage with the driveshaft when the bore receives the driveshaft.

20 Claims, 8 Drawing Sheets

(56) References Cited

U.S. PATENT DOCUMENTS

2005/0215984 A1* 9/2005 Umber ............... A61B 17/1644
606/1
2014/0271288 A1* 9/2014 Hawkins .................. F04D 7/08
60/527

* cited by examiner

TWO POSITION MEDICAL HANDPIECE SEAL

CROSS-REFERENCE TO RELATED APPLICATIONS

This application claims the benefit of priority to U.S. Provisional Patent Application Ser. No. 62/910,519, filed on Oct. 4, 2019 and entitled "TWO POSITION STATIC SEAL". This application also claims the benefit of priority to U.S. Provisional Patent Application Ser. No. 62/960,273, filed on Jan. 13, 2020 and entitled "TWO POSITION MEDICAL HANDPIECE SEAL", the contents of both of which are incorporated herein in their entireties.

TECHNICAL FIELD

This document pertains generally, but not by way of limitation, to surgical devices that can be used for various surgical procedures. More specifically, but not by way of limitation, the present application relates to a seal that can be used for a handpiece of a medical device.

BACKGROUND

Occlusions within cavities of patients, such as sinus cavities, can cause a number of issues with a patient. These issues can include, for example, chronic rhinosinusitis, a deviated septum, nasal polyps, or the like. In order to remove these or other types of occlusions within cavities, a physician can use a handpiece, such as a microdebrider or a drill, to remove the occlusion. Microdebriders can be used with a variety implements depending on the procedure being performed. Typically, a microdebrider may oscillate, i.e., moves in a back and forth rotational motion, and can be used in Rhinologic procedures to remove softer tissues of the sinuses. For example, a pre-bent implement having cutting implements can be used when surgery is being performed at difficult to reach surgical sites, such as the aforementioned sinus cavities. Moreover, cutting implements that may facilitate 360-degree rotation can also be used with a single microdebrider. Thus, a single microdebrider can be used for a variety of procedures with a variety of implements. As noted above, a drill may also be used. Typically, a drill may be used in Otologic procedures to remove bone in and around the ear.

Typically, a microdebrider includes a motor, such as a DC motor, coupled with a driveshaft that rotates upon activation of the DC motor. The implements mentioned above couple with the driveshaft and are activated when the driveshaft rotates. As noted above, a single microdebrider can be used with multiple implements.

Between uses, the microdebrider must be reprocessed, which involves sterilizing the microdebrider in harsh environments, such as an industrial washer, a steam autoclave, or a peroxide plasma sterilization process. When a microdebrider is subjected to these harsh environments, the microdebrider can be exposed to high temperatures, steam, chemical cleansing agents, and water in order to sterilize the microdebrider. Often, these processes can be corrosive or damaging to internal components of the microdebrider, primarily bearings, electrical components or other materials sensitive to chemicals, moisture or other aspects of the reprocessing cycles. Thus, these components should be protected from the harsh environment in order to minimize the possibility of premature degradation of the motor and, consequently, the microdebrider itself.

In order to protect the motor along with other components and electronics, a dynamic seal can be placed around the driveshaft. In particular, the dynamic seal can be in contact with the driveshaft and form a seal around the driveshaft such that the motor along with other components and electronics of the microdebrider are protected from the harsh environment during reprocessing. For example, a seal 2 can be provided as shown with reference to FIG. 1.

Figure 1:
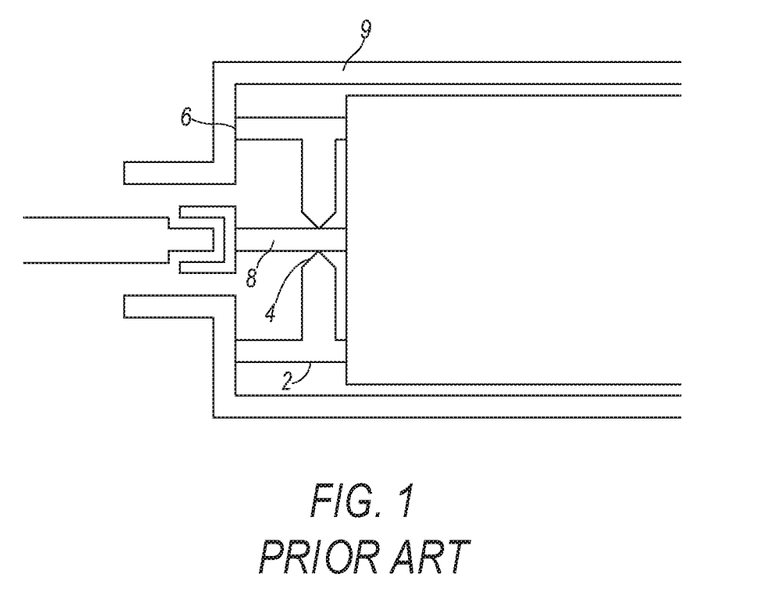
FIG. 1 illustrates a conventional seal for a coupling device.

As may be seen with reference to FIG. 1, the seal 2 includes edges 4 that contact and form a seal with a driveshaft 8. Furthermore, the seal 2 includes edges 6 that contact a handpiece housing 9 and form a seal with the handpiece housing 9. Thus, during reprocessing of device, such as a drill, employing the seal 2, the seal 2, via the seal edges 4 and 6, prevents contaminants from entering a motor of the device. However, the seal edges 4 contact the driveshaft 8 and stay in constant contact with the driveshaft 8. Furthermore, the seal edges 6 stay in constant contact with the handpiece housing 9. Therefore, during operation of the device employing the seal 2, such as during a procedure where a drill is being used, as the driveshaft 8 rotates, which can be at speeds exceeding 70,000 rpms, the seal 2 is sealed against the driveshaft 8. The constant contact between the seal 2 and the driveshaft 8 as the driveshaft 8 rotates at high speeds during use of the device causes degradation of the seal 2 overtime, which allows for the eventual penetration of contaminants into the motor and other components of the device during reprocessing. Moreover, the friction created by the seal 2 against the driveshaft 8 during rotation of the driveshaft 8 creates drag on the driveshaft 8 thereby creating a great amount of heat, which heats a handpiece of the device. In addition, the drag on the driveshaft decreases the efficiency of the motor.

Accordingly, what is needed is a seal which can prevent the passage of contaminants to a motor along with other components of a handpiece used for surgical procedures, such as a microdebrider or a drill. The seal should be able to sealingly engage and disengage with the components of a microdebrider or a drill depending on the state of the microdebrider.

SUMMARY

Examples of the present disclosure relate to a two-position handpiece coupling seal that sealingly engages with a handpiece housing in a first position and couples a handpiece to an implement in a second position. More specifically, when the two-position handpiece coupling seal is in the first position, according to an example, a biasing member of the two-position handpiece coupling seal biases the two-position handpiece coupling seal against a housing of the handpiece. In an example, the two-position handpiece coupling seal can include a first seal that engages with the handpiece housing such that a seal can be formed between the two-position handpiece coupling seal and the handpiece housing when the two-position handpiece coupling seal is in the first position. Therefore, during reprocessing of the handpiece, the seal formed between the first seal and the handpiece housing can prevent the passage of contaminants.

When the handpiece is used during a surgical procedure, the two-position handpiece coupling seal can be configured to couple the handpiece to an implement, such as a burr, in the second position. In an example, when an implement is inserted into the two-position handpiece coupling seal, the implement can move the two-position handpiece coupling seal away from the housing of the handpiece such that the first seal can be spaced apart from the handpiece housing and disengages with the handpiece housing in the second position. In an example, the two-position handpiece coupling seal can couple with a driveshaft of the handpiece such that the handpiece couples with the implement via the two-position handpiece coupling seal. During use of the handpiece, a drive motor can rotate the driveshaft, which in turn can rotate the two-position handpiece coupling seal and the implement since the implement couples with the two-position handpiece coupling seal. Furthermore, since the first seal can be spaced apart from the handpiece housing, the first seal can freely rotate with the two-position handpiece coupling seal and does not suffer from degradation, as discussed above.

DETAILED DESCRIPTION

Examples of the present disclosure relate to a two-position handpiece coupling seal that sealingly engages with a handpiece housing in a first position and couples a handpiece to an implement in a second position. More specifically, when the two-position handpiece coupling seal is in the first position, according to an example, a biasing member of the two-position handpiece coupling seal biases the two-position handpiece coupling seal against a housing of the handpiece. In an example, the two-position handpiece coupling seal can include a first seal that engages with the handpiece housing such that a seal can be formed between the two-position handpiece coupling seal and the handpiece housing when the two-position handpiece coupling seal is in the first position. Therefore, during reprocessing of the handpiece, the seal formed between the first seal and the handpiece housing can prevent the passage of contaminants.

When the handpiece is used during a surgical procedure, the two-position handpiece coupling seal can be configured to couple the handpiece to an implement, such as a burr, in the second position. In an example, when an implement is inserted into the two-position handpiece coupling seal, the implement can move the two-position handpiece coupling seal away from the housing of the handpiece such that the first seal can be spaced apart from the handpiece housing and disengages with the handpiece housing in the second position. In an example, the two-position handpiece coupling seal can couple with a driveshaft of the handpiece such that the handpiece couples with the implement via the two-position handpiece coupling seal. During use of the handpiece, a drive motor can rotate the driveshaft, which in turn can rotate the two-position handpiece coupling seal and the implement since the implement couples with the two-position handpiece coupling seal. Furthermore, since the first seal can be spaced apart from the handpiece housing, the first seal can freely rotate with the two-position handpiece coupling seal and does not suffer from degradation, as discussed above.

Figure 2:
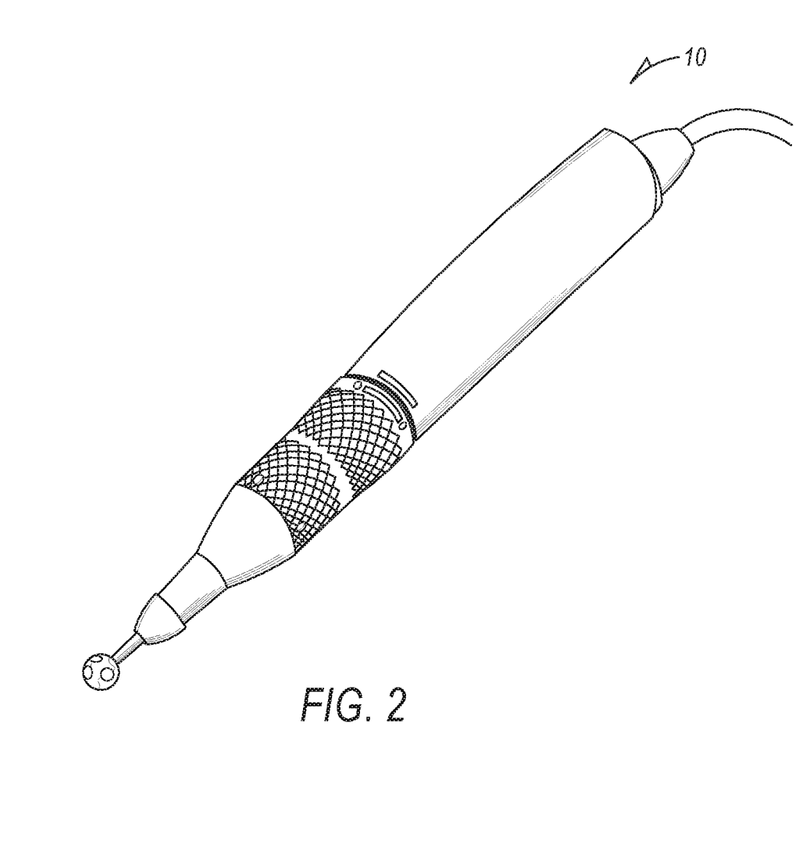
FIGS. 2 and 3 illustrate a device that can be used with a two-position handpiece coupling seal in accordance with at least one example of the present disclosure.
Figure 3:
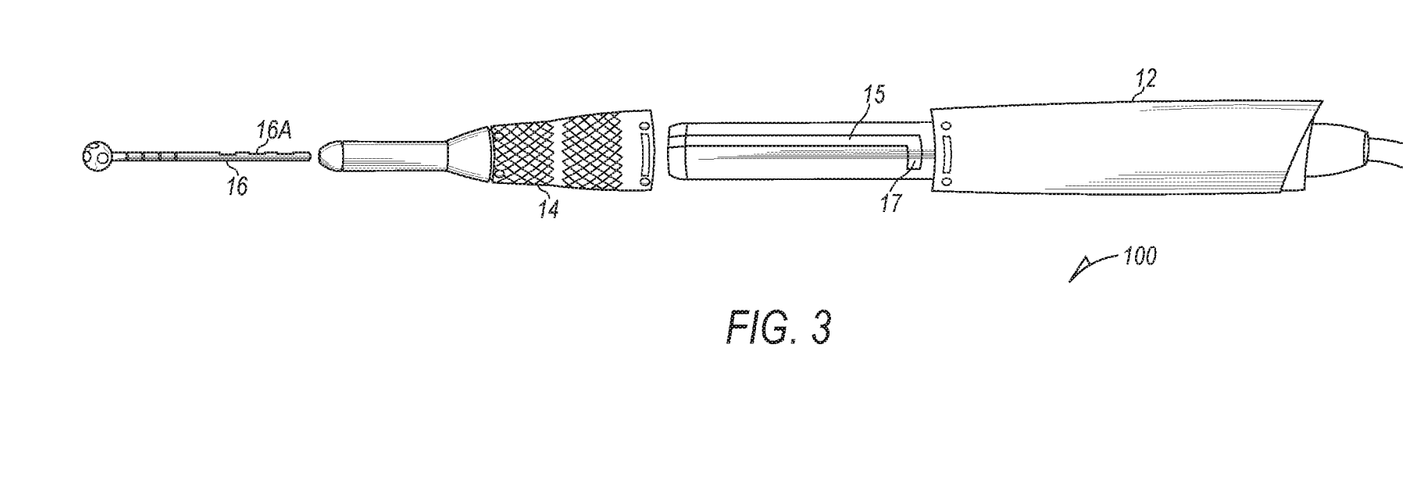

Now making reference to the Figures, and more specifically FIGS. 2 and 3, a device 10 is shown that that can be used in accordance with examples of the present disclosure. The device 10 can be any type of surgical tool that can be used for resection. Examples include a microdebrider, the Diego Elite™ High Speed Drill available from Olympus Medical Systems having a United States headquarters in Center Valley, Pa., or any other type of handpiece that can be used for resection. In an example, the device 10 can include a handpiece 12, an attachment 14, and an implement 16. The attachment 14 can facilitate the coupling of the implement 16 to the handpiece 12. More specifically, the implement 16 can include notches 16A which are configured to engage with complementary notches (not shown) disposed within the attachment 14. Furthermore, in an example, the attachment 14 can lock onto the handpiece 12 via a track 15. In particular, the attachment 14 can include an engagement means (not shown) that can slidingly engage with the track 15. Moreover, the attachment 14 can be locked onto the handpiece 12 when the engagement means slides into a track portion 17 of the track 15 by twisting the attachment 14.

In accordance with an example, when the handpiece 12 is a drill, the drill can have a solid core construction and the implement 16 can be solid core, such as any type of drill bit that can be used for tissue resection or any type of drill blade that can also be used for tissue resection. For example, the implement 16 can be a titanium nitride (TIN) coated variable-length cutting burr, a standard cutting diamond burr, a variable length diamond burr, a diamond stapes burr, or the like. Moreover, in an embodiment when the handpiece 12 is a microdebrider, the microdebrider can have an aspiration pathway, the implement 16 can be cannulated, such as any type of shaver blade. In an example, the implement 16 can couple with the handpiece 12 via a two-position handpiece coupling seal 32, as shown with reference to FIG. 4. Moreover, the implement 16 can be a blade that cuts tissue in a reciprocal motion, such as in a proximal-distal direction. Moreover, the blades can have additional electrosurgical/RF functionality or can incorporate hardware to navigate and/or track the instrument tip while operating.

Figure 4:
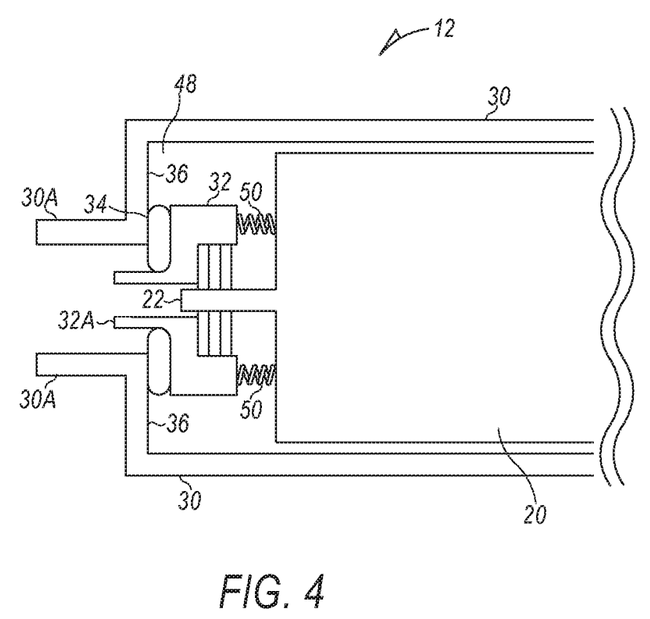
FIG. 4 shows a two-position handpiece coupling seal disposed within a handpiece in a first position in accordance with at least one example of the present disclosure.

Making reference to FIG. 4, the two-position handpiece coupling seal 32 can be disposed within the handpiece 12 of the device 10. In addition, a motor 20 that can power a driveshaft 22 such that the driveshaft 22 rotates is disposed within the handpiece 12. As may be seen with reference to FIG. 4, the driveshaft 22 can attach to the two-position handpiece coupling assembly 32 such that as the driveshaft 22 rotates, the two-position handpiece coupling assembly 32 also rotates. In this example, the two-position handpiece coupling seal 32 can be in a first position where the device 10 is not being used to perform a surgical procedure. Instead, when the two-position handpiece coupling seal 32 is in this position, the device 10 can be subjected to reprocessing, as discussed above. In particular, the two-position handpiece coupling seal 32 includes a first seal 34 that abuts a surface 36 of the handpiece housing 30 in the first position. In an example, the first seal 34 sealingly engages with the handpiece housing surface 36 such that a seal can be formed between the first seal 34 and the handpiece housing surface 36.

Figure 5:
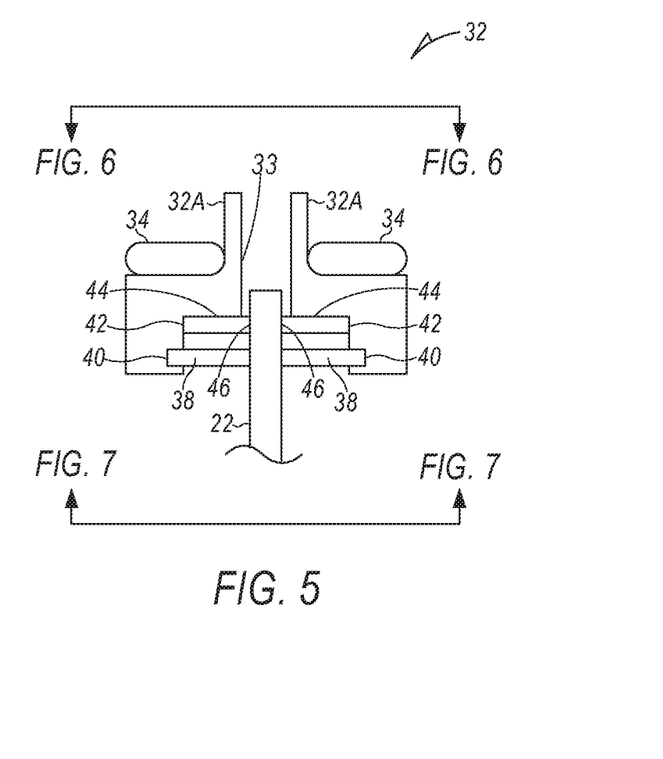
FIG. 5 shows a two-position handpiece coupling seal in accordance with at least one example of the present disclosure.

Now making reference to FIG. 5, the first seal 34 can be disposed at a first end of the two-position handpiece coupling seal 32 around a neck 32A. In an example, the two-position handpiece coupling seal 32 couples with the driveshaft 22 via a driveshaft pin 38. In particular, the driveshaft 22 extends into the two-position handpiece coupling seal 32 via a bore 33 of the two-position handpiece coupling seal 32 such that the two-position handpiece coupling seal 32 couples with the motor 20 via the driveshaft 22. The driveshaft pin 38 extends from the driveshaft 22 in a perpendicular direction relative to the driveshaft 22 as shown with reference to FIG. 5. The two-position handpiece coupling seal 32 can include a recess 40 at the bore 33 that can be configured to receive the driveshaft pin 38 when the driveshaft 22 couples with the two-position handpiece coupling seal 32. As such, the driveshaft 22 can be locked into place when the driveshaft pin 38 is disposed within the two-position handpiece coupling seal recess 40.

The two-position handpiece coupling seal 32 also includes a second seal 42 disposed within a recess 44 of the two-position handpiece coupling seal 32 at a second end of the two-position handpiece coupling seal 32 opposite the first end. As may be seen with reference to FIG. 5, the second seal 42 sealingly engages with a surface 46 of the driveshaft 22. Similar to the first seal 34, the second seal 42 engages with the driveshaft surface 46 such that a seal can be formed between the second seal 42 and the driveshaft surface 46.

In an example, the first seal 34 can couple with the two-position handpiece coupling seal 32 and, as previously mentioned, the second seal 42 can couple with the driveshaft 22. In accordance with an example, when the driveshaft 22 and the two-position handpiece coupling seal 32 rotate, the first seal 34 rotates with the two-position handpiece coupling seal 32 while the second seal 42 rotates with the driveshaft 22. Thus, the problems created by the seal 2 discussed above are avoided since neither the first seal 34 nor the second seal 42 are in static contact with dynamic components, i.e., neither of the seals 34 or 42 remain stationary while in contact with a moving component.

Returning attention to FIG. 4, the handpiece 12 also includes biasing members 50 that are disposed between the motor 20 and the two-position handpiece coupling seal 32, as shown with reference to the Figure. In an example, the biasing members 50 abut the second end of the two-position handpiece coupling seal 32 and bias the two-position handpiece coupling seal 32 into the first position. Thus, the two-position handpiece coupling seal 32 can be configured to abut the biasing members 50. In an example, the biasing members 50 can be compression springs that bias the two-position handpiece coupling seal 32 into the first position such that the first seal 34 sealingly engages with the handpiece housing surface 36 in order to form a seal. While the biasing members 50 are shown as compression springs, any type of biasing technique can be used that moves the two-position handpiece coupling seal 32 into the first position as shown with reference to FIG. 4.

In the first position, when the first seal 34 engages with the handpiece housing surface 36 to form a seal therebetween, during reprocessing of the device 10, contaminants, such as water, chemicals, or the like, are prevented from moving past the first seal 34 and into a chamber 48 of the handpiece 12. Moreover, contaminants are not able to move into the motor 20 nor other components of the device 10 within the handpiece 12, such as bearings, electrical components or other materials sensitive to chemicals, moisture or other aspects of the reprocessing cycles. Likewise, since the second seal 42 sealingly engages with the driveshaft surface 46, contaminants are not able to move into the chamber 48, the motor 20, or other components within the handpiece 12.

In an example, the first seal 34 can be formed from any type of material that is immune to heat, chemicals, and the hard environment that the device 10 is subjected to during reprocessing, as discussed above. For example, the first seal 34 can be formed from an elastomer, Teflon™, or the like. Furthermore, the first seal 34 can be an o-ring, a face seal, or have any type of geometry that lends itself to providing a sealing engagement between the first seal 34 and the handpiece housing surface 36. In an example, the second seal 42 can be formed from any type of material that is immune to heat, chemicals, and the hard environment that the device 10 is subjected to during reprocessing, as discussed above. For example, the second seal 42 can be formed from an elastomer, Teflon™, or the like. Furthermore, the second seal 42 can be an o-ring, a face seal, or have any type of geometry that lends itself to providing a sealing engagement between the second seal 42 and the driveshaft surface 46.

Figure 6:
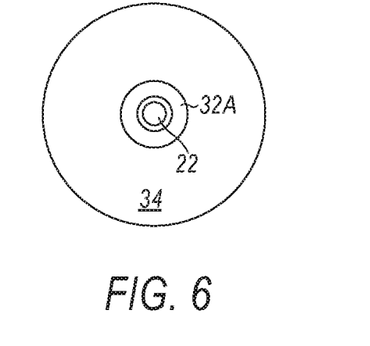
FIG. 6 is a top down view of a two-position handpiece coupling seal of FIG. 5 illustrating a circular configuration of a first seal formed around the two-position handpiece coupling seal, in accordance with at least one example of the present disclosure.
Figure 7:
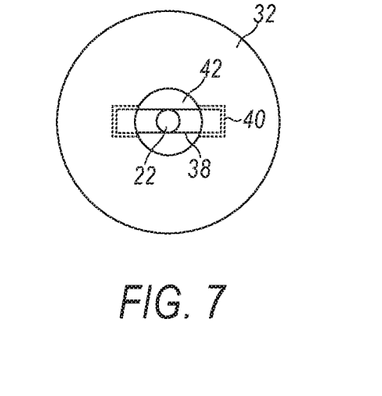
FIG. 7 is a bottom view of the two-position handpiece coupling seal shown with reference to FIG. 5 in accordance with at least one example of the present disclosure.

FIGS. 6 and 7 respectively illustrate top and bottom views of the two-position handpiece coupling seal 32 shown with reference to FIG. 5 in accordance with examples of the present disclosure. In particular, FIG. 6 is a top down view of the two-position handpiece coupling seal 32 illustrating the circular configuration of the first seal 34 formed around the two-position handpiece coupling seal 32. In particular, the first seal can 34 completely surround the neck 32A of the two-position handpiece coupling seal 32. Accordingly, when the two-position handpiece coupling seal 32 is in the first position shown with reference to FIG. 4, contaminants, such as water, chemical agents, and the like cannot get into the chamber 48 nor the motor 20 along with other components of the device 10.

FIG. 7 is a bottom view of the two-position handpiece coupling seal 32 shown with reference to FIG. 5. As may be seen with reference to FIG. 7, the second seal 42 can completely surround the driveshaft 22. Thus, when the two-position handpiece coupling seal 32 is in the first position shown with reference to FIG. 4, contaminants, such as water, chemical agents, and the like cannot get into the chamber 48 nor the motor 20 along with other components of the device 10.

Figure 8:
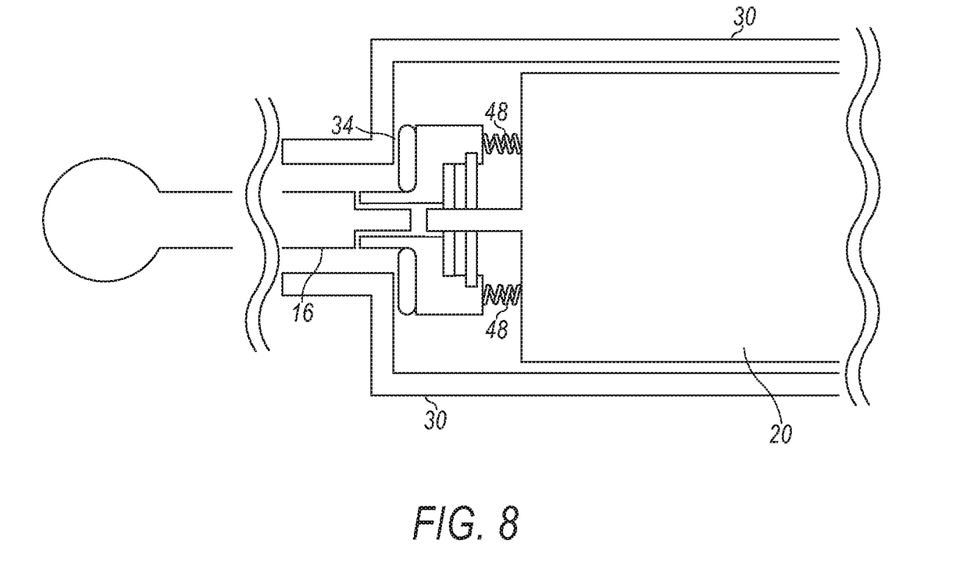
FIG. 8 illustrates a two-position handpiece coupling seal disposed within a handpiece in a second position in accordance with at least one example of the present disclosure.

When the implement 16 is coupled with the two-position handpiece coupling seal 32, the two-position handpiece coupling seal 32 can move into a second position, as shown with reference to FIG. 8. In particular, the implement 16 can bias the first seal 42 along with the two-position handpiece coupling seal 32 away from the housing 30 and the handpiece housing surface 36. As previously discussed, the implement notches 16A can engage with complementary notches in the attachment 14. Furthermore, as discussed above, the attachment 14 can lock onto the handpiece 12 via the track 15 and the track portion 17, thereby biasing the two-position handpiece coupling seal 32 into the second position as shown with reference to FIG. 8. In an example, when the attachment is locked into the handpiece 12 while the implement 16 is engaged with the attachment 14, the implement 16 couples with the two-position handpiece coupling seal 32, as shown with reference to FIG. 9.

Figure 9:
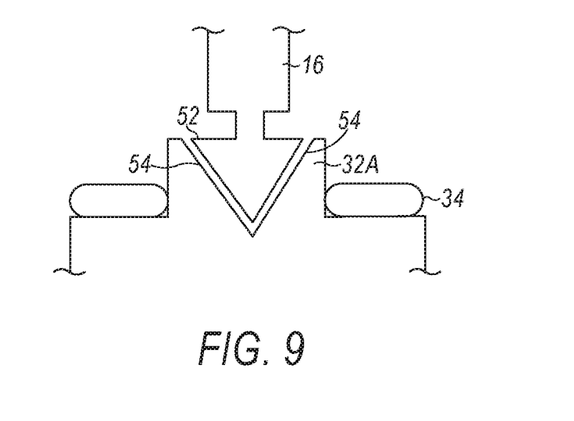
FIG. 9 shows the coupling of an implement with a two-position handpiece coupling seal in accordance with at least one example of the present disclosure.

Now making reference to FIG. 9, the implement 16 can include a coupling member 52, which, in this example, has a triangular configuration. However, it should be noted that the implement coupling member 52 can have any number of configurations, including a rectangular configuration or the like. The two-position handpiece coupling seal 32 can include an implement coupling member recess 54 disposed within the neck 32A of the two-position handpiece coupling seal 32. In an example, the implement coupling member recess 54 has a configuration that complements the configuration of the implement coupling member 52. In an example, the implement coupling member 52 has a triangular configuration. Thus, in this example, the implement coupling recess 52 of the two-position handpiece coupling seal 32 also has a triangular configuration that compliments the triangular configuration of the implement coupling member 52 such that the implement coupling recess 52 holds the implement coupling member 52. in place during operation of the device 10. When the implement 16 is engaged with the attachment 14 and the attachment 14 is locked onto the handpiece 12, the implement coupling member 52 can engage with the implement coupling member recess 54. Furthermore, in this configuration, when the attachment 14 is locked onto the handpiece 12, the implement 16 can bias the two-position handpiece coupling seal 32 as shown with reference to FIG. 8. Moreover, the neck 32A of the two-position handpiece coupling seal 32 can extend into a neck 30A of the handpiece housing 30, thereby facilitating further coupling of the implement 16 with the two-position handpiece coupling seal 32.

Returning attention to FIG. 8, when the implement 16 couples with the two-position handpiece coupling seal 32, the two-position handpiece coupling seal 32 can clear the handpiece housing surface 36 such that the first seal 34 no longer contacts the handpiece housing surface 36. Moreover, neither the two-position handpiece coupling seal 32 nor the first seal 34 contact the handpiece housing 30 such that the two-position handpiece coupling seal 32 freely rotates within the handpiece housing 30.

When a surgeon uses the device 10 during a procedure, such as removing an occlusion, the motor 20 rotates the driveshaft 22. As the driveshaft 22 rotates, the two-position handpiece coupling seal 32 also rotates. Furthermore, as discussed above, the first seal 34 and the second seal 42 rotate with the driveshaft 22 and the two-position handpiece coupling seal 32. However, since the first seal 34 does not contact the handpiece housing surface 36 or the handpiece housing 30, the first seal 42 is not subjected to the problems discussed above with respect to the seal 2. Furthermore, the second seal 42 remains statically engaged with the driveshaft 22 such that the second seal 42 rotates with the driveshaft 22. Since the second seal 42 rotates with the driveshaft 22, the second seal 42 also does not experience the problems discussed above with respect to the seal 2.

Figure 10:
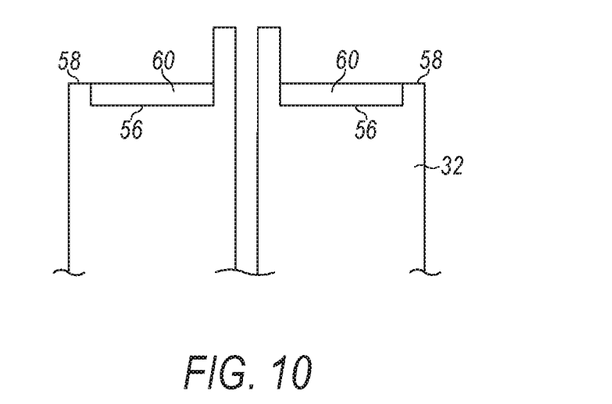
FIGS. 10 and 11 illustrate seals for a two-position handpiece coupling seal in accordance with at least one example of the present disclosure.

In addition to the configuration previously discussed with reference to FIGS. 4-9 and the first seal 34, the two-position handpiece coupling seal 32 can include seals having a different configuration, as shown with reference to FIGS. 10 and 11. FIG. 10 illustrates a seal that can be used with the two-position handpiece coupling seal 32 in accordance with an alternative example of the present disclosure. In this example, the two-position handpiece coupling seal 32 can include a seal recess 56 that defines a lip 58 around the neck 32A. In an example, the seal recess can hold a seal 60 such that when the two-position handpiece coupling seal 32 is in the first position discussed above with reference to FIG. 4, the seal 60 can sealingly engage with the handpiece housing surface 36 of the housing 30 and form a seal therewith. As may be seen with reference to FIG. 10, the seal 60 has a planar configuration such that an entire surface of the seal 60 engages with the handpiece housing surface 36 similar to the first seal 34 shown with reference to FIG. 4. Furthermore, the seal between the seal 60 and the handpiece surface 36 can prevent contamination of the chamber 48 and the motor 20, as discussed above. In an example, the seal 60 can be formed from an elastomer, Teflon™, or the like. Furthermore, the seal 60 can be an o-ring, a face seal, or the like.

Figure 11:
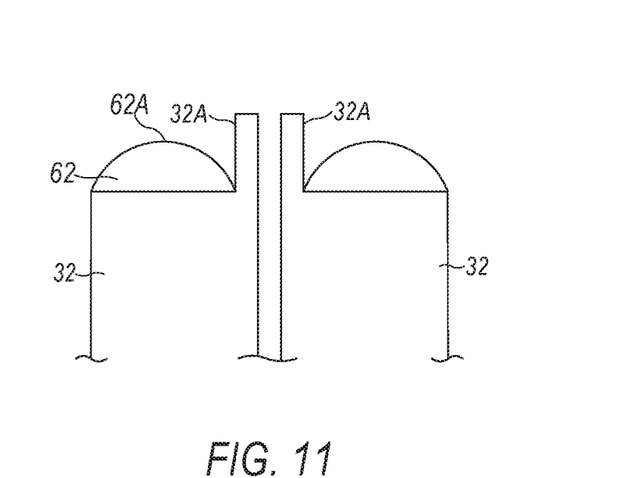

FIG. 11 illustrates a seal 62 in accordance with a further example of the present disclosure. Here, the seal 62 can be disposed on the two-position handpiece coupling seal 32 and completely surrounds the neck 32A of the two-position handpiece coupling seal 32. In this embodiment, the seal 62 has a semi-tubular configuration where the seal 62 includes a top portion 62A that can extend from the seal 62, as shown with reference to FIG. 11. In an embodiment, when the seal 62 is used, the top portion 62A of the seal 62 is compressed against the handpiece housing surface 36 thereby forming a seal with the handpiece housing surface 36 similar to the first seal 34 shown with reference to FIG. 4. Similar to the seals 34, 42, and 60, the seal 62 can be formed from an elastomer, Teflon™, or the like. In addition, the first seal 62 can be an o-ring, a face seal, or the like.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. §

What is claimed is:

1. A device comprising:
   a handpiece having a housing;
   a two-position handpiece coupling seal within the housing, the two-position handpiece coupling seal including:
   a neck disposed at a first end of the two-position handpiece coupling seal, the neck being configured to receive an implement;
   a first seal disposed about the neck of the two-position handpiece coupling seal; and
   a second seal disposed about a bore of the two-position handpiece coupling seal at a second end of the two-position handpiece coupling seal opposite the first end, wherein the bore is configured to receive a driveshaft and the second seal is configured to sealingly engage with the driveshaft when the bore receives the driveshaft; and
   a biasing member that abuts the second end of the two-position handpiece coupling seal, wherein:
   the biasing member is configured to bias the two-position handpiece coupling seal into a first position where the first seal sealingly engages with a surface of the housing; and
   the two-position handpiece coupling seal is configured to be in a second position when the neck receives the implement, wherein when the neck and the first seal are in the second position, the first seal is spaced away from the surface of the housing in the second position.

2. The device of claim 1, wherein the two-position handpiece coupling seal further comprises a recess at the bore where the recess is configured to receive a driveshaft pin of the driveshaft when the bore receives the driveshaft.

3. The device of claim 2, wherein the device further comprises a motor and the driveshaft extends from the motor to the two-position handpiece coupling seal such that the two-position handpiece coupling seal couples with the motor when the two-position handpiece coupling seal receives the driveshaft at the bore.

4. The device of claim 2, wherein when the neck receives the implement, the two-position handpiece coupling seal is configured to move to the second position where the first seal is spaced away from the surface of the housing.

5. The device of claim 4, wherein when a motor coupled with the driveshaft rotates the driveshaft during operation of the device, the two-position handpiece coupling seal, the first seal, and the second seal rotate with the driveshaft.

6. The device of claim 1, wherein the neck comprises an implement coupling member recess configured to receive the implement.

7. The device of claim 6, wherein the implement coupling member recess has a triangular configuration.

8. The device of claim 1, wherein the biasing member is a compression spring.

9. A two-position handpiece coupling seal comprising:
   a neck extending from a first end of the two-position handpiece coupling seal, the neck being configured to receive an implement;
   a first seal extending around an outer surface of the neck;
   a second seal disposed about a bore extending through the neck from the first end of the two-position handpiece coupling seal to a second end of the two-position handpiece coupling seal opposite the first end, wherein the bore is configured to receive a driveshaft and the second seal is configured to sealingly engage and rotate with the driveshaft when the bore receives the driveshaft; and
   a biasing member that abuts the second end of the two-position handpiece coupling seal, wherein:
   the biasing member is configured to bias the two-position handpiece coupling seal into a first position where the first seal sealingly engages with a housing surface in the first position; and
   the two-position handpiece coupling seal is configured to be in a second position when the neck receives the implement, wherein when the neck receives the implement, the two-position handpiece coupling seal is configured to move to the second position where the first seal is spaced away from the housing surface.

10. The two-position handpiece coupling seal of claim 9, wherein the two-position handpiece coupling seal further comprises a recess at the bore where the recess is configured to receive a driveshaft pin of the driveshaft when the bore receives the driveshaft.

11. The two-position handpiece coupling seal of claim 9, wherein the neck comprises an implement coupling member recess configured to receive the implement.

12. The two-position handpiece coupling seal of claim 11, wherein the implement coupling member recess has a triangular configuration.

13. The two-position handpiece coupling seal of claim 9, wherein the first seal and the second seal are configured to rotate with the driveshaft when the driveshaft rotates.

14. The two-position handpiece coupling seal of claim 9, wherein the two-position handpiece coupling is configured to abut a biasing member, where the biasing member is configured to move the two-position handpiece coupling between a first position and a second position.

15. The two-position handpiece coupling seal of claim 14, wherein the biasing member is a compression spring.

16. The two-position handpiece coupling seal of claim 9, wherein the two-position handpiece coupling further comprises a lip disposed about the first seal, where the lip defines a recess within which the first seal sits.

17. A device comprising:
   a handpiece having a housing;
   a two-position handpiece coupling seal within the housing, the two-position handpiece coupling seal including:
   a neck disposed at a first end of the two-position handpiece coupling seal, the neck comprising an implement coupling member recess configured to receive an implement;
   a first seal disposed about the neck of the two-position handpiece coupling seal; and
   a second seal disposed about a bore of the two-position handpiece coupling seal at a second end of the two-position handpiece coupling seal opposite the first end, wherein the bore is configured to receive a driveshaft and the second seal is configured to sealingly engage with the driveshaft when the bore receives the driveshaft; and a biasing member that abuts the second end of the two-position handpiece coupling seal, wherein:

the biasing member is configured to bias the two-position handpiece coupling seal into a first position where the first seal sealingly engages with a surface of the housing in the first position; and the two-position handpiece coupling seal is configured to be in a second position when the neck receives the implement, wherein when the neck receives the implement, the two-position handpiece coupling seal is configured to move to the second position where the first seal is spaced away from the surface of the housing.

18. The device of claim 17, wherein the device further comprises a motor and the driveshaft extends from the motor such that the two-position handpiece coupling seal couples with the motor when the two-position handpiece coupling seal receives the driveshaft at the bore.

19. The device of claim 18, wherein the motor rotates the driveshaft during operation of the device and the two-position handpiece coupling seal, the first seal, and the second seal rotate with the driveshaft.

20. The device of claim 17, wherein the two-position handpiece coupling seal further comprises a recess at the bore where the recess is configured to receive a driveshaft pin of the driveshaft when the bore receives the driveshaft.

* * * * *